(12) United States Patent
Davidowski et al.

(10) Patent No.: US 9,707,365 B2
(45) Date of Patent: Jul. 18, 2017

(54) CONDENSATION REDUCTION AND MANAGEMENT SYSTEMS IN A GAS FLOW DELIVERY SYSTEM

(71) Applicant: RIC INVESTMENTS, LLC, Wilmington, DE (US)

(72) Inventors: Doug L Davidowski, Champaign, IL (US); Peter Chi Fai Ho, Pittsburgh, PA (US); Lance Ranard Busch, Trafford, PA (US); Richard Joseph Lordo, Butler, PA (US); Jerome Matula, Jr., Apollo, PA (US)

(73) Assignee: RIC INVESTMENTS, LLC, Wilmington, DE (US)

( * ) Notice: Subject to any disclaimer, the term of this patent is extended or adjusted under 35 U.S.C. 154(b) by 63 days.

(21) Appl. No.: 14/284,885

(22) Filed: May 22, 2014

(65) Prior Publication Data
US 2014/0251336 A1 Sep. 11, 2014

Related U.S. Application Data

(62) Division of application No. 11/300,052, filed on Dec. 14, 2005, now Pat. No. 8,757,150.
(Continued)

(51) Int. Cl.
*A61M 16/06* (2006.01)
*A61M 16/08* (2006.01)
*A61M 16/00* (2006.01)

(52) U.S. Cl.
CPC .... *A61M 16/0622* (2014.02); *A61M 16/0057* (2013.01); *A61M 16/06* (2013.01);
(Continued)

(58) Field of Classification Search
CPC ....... A41D 13/1176; A61F 5/08; A61G 13/12; A61G 13/121; A61G 2200/325; A61M 15/0015; A61M 15/0018; A61M 16/0048; A61M 16/0057; A61M 16/0069; A61M 16/009; A61M 16/0447; A61M 16/0456; A61M 16/06; A61M 16/0616; A61M 16/0622; A61M 16/0633; A61M 16/0638;
(Continued)

(56) References Cited

U.S. PATENT DOCUMENTS

| 302,949 A | 8/1884 | Skene |
| 1,914,418 A * | 6/1933 | Goyena ..................... A61F 5/08 128/206.18 |

(Continued)

OTHER PUBLICATIONS

Dupont, "Thermolite® Base Performance Fabrics", http://www.fabriclink.com/PK/Thermolie/home.html, 2004.

*Primary Examiner* — Annette Dixon
(74) *Attorney, Agent, or Firm* — Michael W. Haas

(57) ABSTRACT

Condensation management techniques for a gas flow delivery system. The techniques include providing a radiant barrier associated with patient circuit and/or a patient interface, providing a water trap and/or an absorbent insert in the patient interface device, or a combination of these techniques. The radiant barrier prevents condensation from forming in the patient circuit and/or the patient interface. The water trap and absorbent insert in the patient interface control condensation that reaches or forms in the interior of the patient interface to prevent it from interfering the user of the gas delivery system.

6 Claims, 16 Drawing Sheets

Related U.S. Application Data

(60) Provisional application No. 60/637,339, filed on Dec. 17, 2004.

(52) U.S. Cl.
CPC .... *A61M 16/0616* (2014.02); *A61M 16/0633* (2014.02); *A61M 16/0808* (2013.01); *A61M 16/0875* (2013.01)

(58) Field of Classification Search
CPC .......... A61M 16/0666; A61M 16/0683; A61M 16/0688; A61M 16/08; A61M 16/0816; A61M 16/0875; A61M 16/104; A61M 16/1055; A61M 16/1065; A61M 16/107; A61M 16/1075; A61M 16/109; A61M 16/12; A61M 16/16; A61M 16/208; A61M 2205/42; A61M 2205/43; A61M 2205/582; A61M 2205/583; A61M 2205/8206; A61M 2210/0618; A62B 18/00; A62B 18/02; A62B 18/025; A62B 18/08; A62B 18/084; A62B 18/10; A62B 23/025; A62B 23/06; Y10S 128/91; Y10S 128/912; Y10S 55/13; Y10S 55/35
USPC ............ 128/200.24, 201.23, 202.11, 202.27, 128/202.28, 202.29, 203.11, 203.29, 128/204.17, 204.18, 205.12, 205.24, 128/205.25, 205.27, 206.12, 206.15, 128/206.16, 206.17, 206.18, 206.21, 128/206.24, 206.25, 206.26, 206.27, 128/206.28, 207.11, 207.12, 207.13, 128/207.14, 207.16, 207.18, 846, 909, 128/910, 912
See application file for complete search history.

(56) References Cited

U.S. PATENT DOCUMENTS

| | | | |
|---|---|---|---|
| 2,005,072 A | 6/1935 | Booharin | |
| 2,201,315 A | 5/1940 | Lehmberg | |
| 2,382,364 A | 8/1945 | Yant | |
| 2,426,161 A | 8/1947 | Biederman | |
| 2,435,721 A | 2/1948 | Lehmann | |
| 2,845,927 A * | 8/1958 | Hill | A62B 23/025 128/206.17 |
| 3,099,987 A | 8/1963 | Bartlett, Jr. | |
| 3,316,904 A | 5/1967 | Wall | |
| 3,638,926 A | 2/1972 | Melville | |
| 4,071,026 A | 1/1978 | Bevins | |
| 4,196,728 A | 4/1980 | Granite | |
| 4,232,667 A | 11/1980 | Chalon | |
| 4,333,451 A | 6/1982 | Paluch | |
| 4,355,637 A | 10/1982 | Dyer | |
| 4,377,164 A | 3/1983 | Sabbota | |
| 4,458,679 A | 7/1984 | Ward | |
| 4,632,108 A * | 12/1986 | Geil | A61L 29/126 128/207.14 |
| 4,701,965 A * | 10/1987 | Landis | A41D 13/11 128/857 |
| 4,751,924 A | 6/1988 | Hammerschmidt | |
| 4,850,347 A | 7/1989 | Skov | |
| 4,964,404 A | 10/1990 | Stone | |
| 5,004,018 A | 4/1991 | Bainbridge | |
| 5,027,812 A | 7/1991 | Shapiro | |
| 5,065,757 A | 11/1991 | Dragisic | |
| 5,103,816 A | 4/1992 | Kirschbaum | |
| 5,143,060 A | 9/1992 | Smith | |
| 5,228,435 A | 7/1993 | Smith | |
| 5,228,436 A | 7/1993 | Parkin | |
| 5,355,878 A * | 10/1994 | Griffiths | A62B 18/084 128/201.23 |
| 5,360,002 A | 11/1994 | Smith | |
| 5,377,670 A | 1/1995 | Smith | |
| 5,400,602 A | 3/1995 | Chang | |
| 5,469,864 A | 11/1995 | Rosenblatt | |
| 5,476,121 A | 12/1995 | Yoshikawa | |
| 5,524,642 A | 6/1996 | Rosenblatt | |
| 5,558,084 A | 9/1996 | Daniell | |
| 5,558,088 A | 9/1996 | Smith | |
| 5,595,173 A | 1/1997 | Dodd | |
| 5,623,922 A | 4/1997 | Smith | |
| 5,673,687 A | 10/1997 | Dobson | |
| 5,735,266 A | 4/1998 | Smith | |
| 5,794,617 A * | 8/1998 | Brunell | A62B 18/084 128/206.12 |
| 5,947,116 A | 9/1999 | Gamow | |
| 6,095,505 A | 8/2000 | Miller | |
| 6,201,223 B1 | 3/2001 | Nitta | |
| 6,330,883 B1 | 12/2001 | Berger | |
| 6,391,237 B1 | 5/2002 | Kearney | |
| 6,397,846 B1 | 6/2002 | Skog | |
| 6,467,482 B1 * | 10/2002 | Boussignac | A61M 16/06 128/206.24 |
| 6,490,737 B1 * | 12/2002 | Mazzei | A61G 13/12 128/846 |
| 6,536,428 B1 | 3/2003 | Smith | |
| 6,550,476 B1 | 4/2003 | Ryder | |
| 6,615,834 B2 | 9/2003 | Gradon | |
| 6,851,429 B2 * | 2/2005 | Bishop | A41D 13/1176 128/205.25 |
| 6,860,268 B2 | 3/2005 | Bohn | |
| 6,905,566 B1 | 6/2005 | Pitzer | |
| 7,086,422 B2 | 8/2006 | Huber et al. | |
| 7,290,546 B2 * | 11/2007 | Sprinkle | A61M 16/06 128/206.24 |
| 2002/0185134 A1 * | 12/2002 | Bishop | A41D 13/1176 128/206.25 |

* cited by examiner

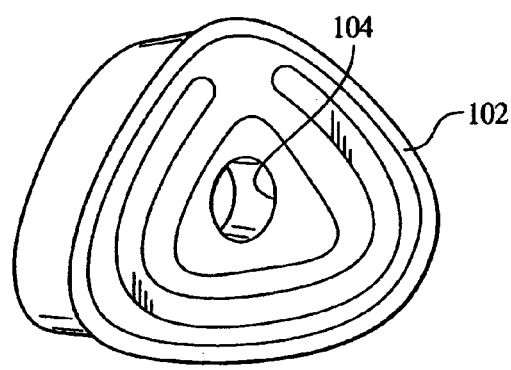
FIG. 27
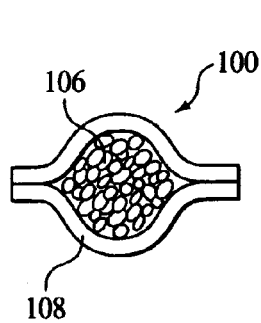 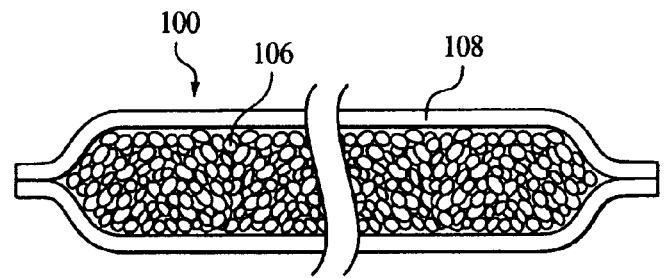
FIG. 28　　　　　　FIG. 29
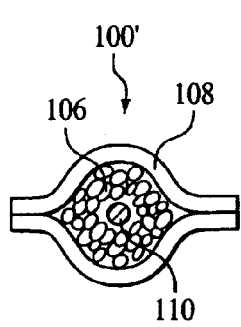 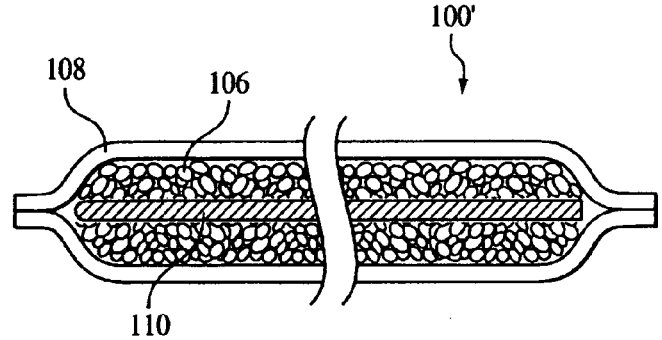
FIG. 30　　　　　　FIG. 31

CONDENSATION REDUCTION AND MANAGEMENT SYSTEMS IN A GAS FLOW DELIVERY SYSTEM

CROSS-REFERENCE TO RELATED APPLICATIONS

This application is a Divisional under 35 U.S.C. §120 of U.S. patent application Ser. No. 11/300,052, filed Dec. 14, 2005, now U.S. Pat. No. 8,757,150, which claims priority under 35 U.S.C. §119(e) from provisional U.S. patent application No. 60/637,339, filed Dec. 17, 2004, the contents of which are incorporated herein by reference.

BACKGROUND OF THE INVENTION

1. Field of the Invention

The present invention relates to a system for isolating, controlling, or reducing condensation in a patient circuit or in a patient interface in a gas flow delivery system.

2. Description of the Related Art

Gas flow delivery systems are used to deliver a flow of gas to an airway of a subject. Such systems are typically used in the medical field to deliver gas to a patient. Examples of gas flow delivery systems in the medical field include a ventilator or respirator, which replaces or supplements a patient's respiration, and a pressure support system, which provides a flow of gas to an airway of a patient at an elevated pressure to treat a medical disorder, such as obstructive sleep apnea (OSA). Pressure support systems include, but are not limited to continuous positive airway pressure (CPAP) devices, which delivers a constant positive pressure to the airway of a patient over multiple respiratory cycles, and variable pressure devices where the pressure of the flow of gas delivered to the patient is variable.

Variable pressure devices include auto-titrating devices that are capable of changing a base pressure or pressure profile delivered to the patent based on a monitored condition of the patient. Other variable pressure devices change the pressure of the flow of gas during a respiratory cycle. These devices include the following: a proportional assist ventilation (PAV®), a proportional positive airway pressure (PPAP®) device, a C-Flex™ device, a Bi-Flex™ device, and a BiPAP® device manufactured and distributed by Respironics, Inc. of Pittsburgh, Pa. The BiPAP device is a bi-level pressure support system in which the pressure provided to the patient varies with the patient's respiratory cycle so that a higher pressure is delivered during inspiration than during expiration.

A typical gas flow delivery system comprises a pressure/flow generating system that produces a flow of gas for delivery to a patient and a system for communicating the flow of gas to the patient. The latter system typically includes a flexible conduit having one end coupled to the pressure/flow generating device and a second end portion that couples to an airway of patient through a patient interface. The conduit, which is also referred to as a patient circuit, carries the flow of gas from the pressure generating device during operation of the system. The patient interface device, typically in the form of a nasal, oral, or nasal/oral mask, is coupled to the second end portion of the conduit to communicate the flow of gas from the patient circuit to the airway of the patient.

Heated humidifiers have been developed for use with gas delivery system devices to humidify the gas supplied to the patient. A typical humidifier comprises a heated water reservoir connected in series with the delivery conduit between the flow generator and the patient interface. As the humidified gas moves through the patient circuit from the humidifier to the patient interface, condensation or rainout may from in the patient circuit or in the patient interface device. Condensation will occur if the gas leaving the humidifier is at a saturation level higher than that required to attain saturation at the lower temperature of the patient interface.

Condensation may also build up on the inner surface of the patient circuit and/or the patient interface. The formation of condensation in the patient circuit is not limited to the use of heated humidifiers. Condensation may also form whenever the ambient temperature is colder than the gas temperature of the patient circuit. Condensation may even form in the patient circuit without any form of humidification present, such as in winter.

Condensation in the patient circuit and/or patient interface is undesirable for several reasons. First, liquid in the patient circuit may reach the patient, where it could drip on the patient's face. Moist areas are also more prone to formation of bacteria. Additionally, gas flowing through any accumulated condensation may generate an annoying gurgling sound. To remove the condensation it is necessary for the patient or caregiver to periodically disconnect the patient from the gas flow/pressure generator, for example by removing the mask from the face or disconnecting the patient circuit from the mask or gas flow/pressure generator so that the condensed water can be drained. This process is disruptive and may interfere with the patient's therapy.

SUMMARY OF THE INVENTION

Accordingly, it is an object of the present invention to provide techniques for isolating, controlling, or reducing condensation in a patient circuit and patient interface. This object is achieved according to one embodiment of the present invention by providing a patient circuit that includes a conduit having a first end portion, a second end portion, and a lumen defined therein from the first end portion to the second end portion. A radiant barrier is associated with the conduit such that the radiant barrier is disposed between an ambient environment and the lumen. The radiant barrier is a low emissivity material that reduces heat loss from the conduit due to radiant energy. By reducing radiation heat loss from the conduit, the gas flow in the conduit is not cooled as much as in current systems, which use only an insulation layer to prevent heat loss due to conduction. By reducing the amount of cooling, condensation is reduced.

In another embodiment of the present invention, this object is achieved by providing a patient interface having a shell and an insert member. The shell wall and insert member are sized, configured, and disposed relative to one another such that a gap is defined between the wall of the insert member and a wall of the shell. The gap is positioned such that water entering the interface from the patient circuit is prevented from reaching the patient, but collects in this space. This prevents water or the possible intrusion of water into the patient's airway when the mask is donned by the user. The insert also creates an insulation layer within the interface, much like a double glass window on a home. The warm and humid gas fills the gap between the shell and the attachment, forming an insulating layer to eliminate condensation on the insert member wall facing the patient. Instead, any condensation that may form will do so on the wall of the shell, where it is trapped in the gap between the shell and the insert member.

In yet another embodiment, this object is achieved by providing a system for delivering a breathing gas to a patient that includes a gas flow generating device that produces a flow of gas, a conduit that carries the flow of gas from the gas flow generating device during operation of the system, and a patient interface coupled to the conduit. In addition, an absorbent material is disclosed in the patient interface. In a presently preferred exemplary embodiment of the invention, the absorbent insert comprises a super-absorbent polymer material disposed inside a porous wicking material, such as cloth or paper. The super-absorbent polymer material can absorb water up to 300 times the volume of the absorbent insert. After use, the saturated absorbent insert may be air or oven dried and re-used. The absorbent insert is preferably large enough so that the absorbent insert may not accidentally invade the nasal cavity.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 27 is a rear perspective view of a patient interface that includes an absorbent insert according to the principles of an exemplary embodiment of the present invention;

FIGS. 28 and 29 are a cross-sectional end and side views, respectively of an exemplary embodiment of the absorbent insert of FIG. 27; and FIGS. 30 and 31 are cross-sectional end and side views, respectively, of another embodiment for an absorbent insert.

DETAILED DESCRIPTION OF THE EXEMPLARY EMBODIMENTS

Figure 1:
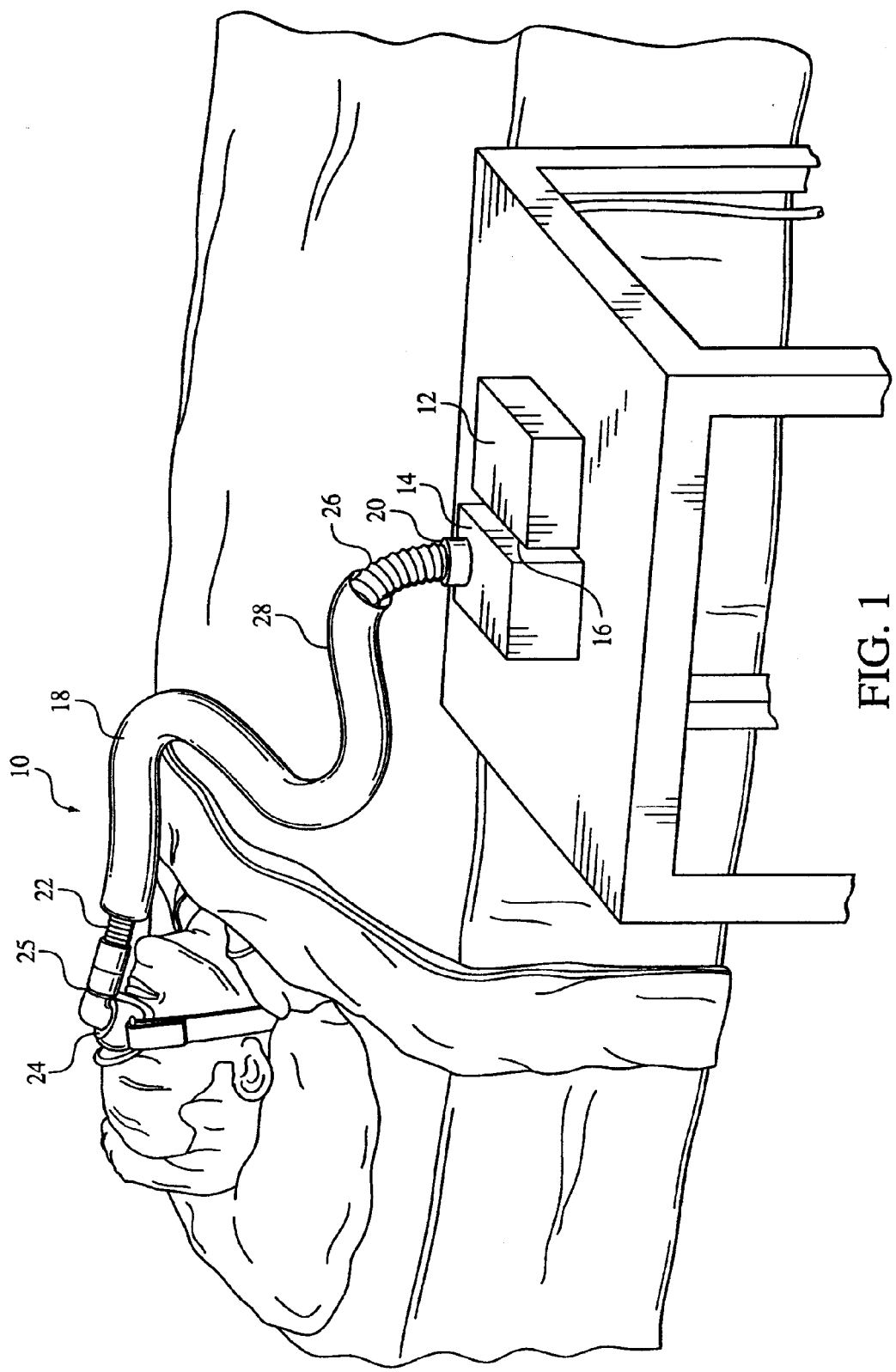
FIG. 1 is a perspective view of a gas flow generating system that includes a patient circuit having a radiant barrier according to the principles of the present invention.
Figure 2:
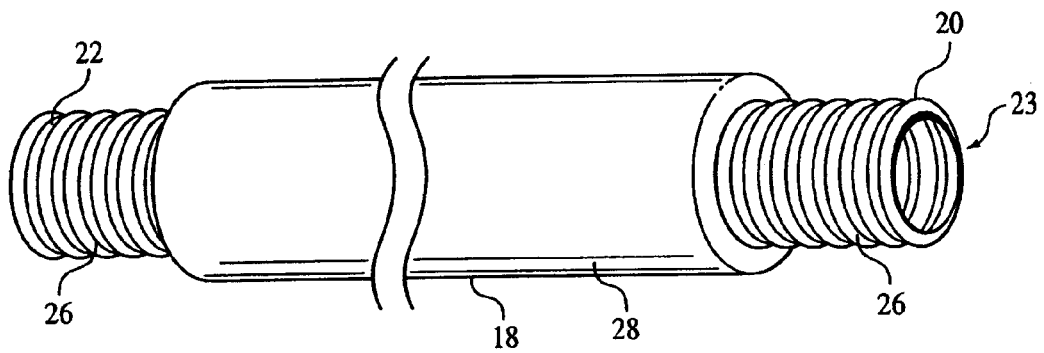
FIG. 2 is a partial cut-away perspective view of the patient circuit of FIG. 1.
Figure 3:
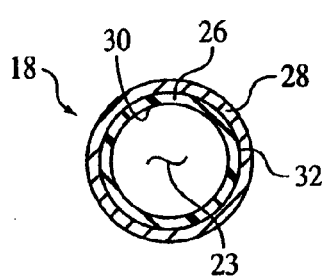
FIG. 3 is a cross-sectional view of the patient circuit of FIG. 2.

Referring first to FIGS. 1-3, a gas flow delivery system 10 for delivering a flow of gas to an airway of a patient is illustrated. Gas flow delivery system 10 comprises a pressure generating device 12 that produces a flow of gas and an optional humidifier 14 coupled to an outlet 16 of the pressure generating device 12. A gas delivery conduit, which is also referred to as a patient circuit, 18 is coupled to the outlet of the humidifier. Of course, if the humidifier is omitted, the patient circuit would be coupled to the outlet of the gas flow generating device.

Pressure generating device 12 is any conventional ventilation or pressure support system. Examples of such systems include, but are not limited to: a ventilator, continuous positive airway pressure (CPAP) device, or a variable pressure device, e.g. an auto-titrating device, proportional assist ventilation (PAV®) device, proportional positive airway pressure (PPAP®) device, C-Flex™ device, Bi-Flex™ device, or a BiPAP® device manufactured and distributed by Respironics, Inc. of Pittsburgh, Pa., in which the pressure provided to the patient varies with the patient's respiratory cycle so that a higher pressure is delivered during inspiration than during expiration, or other pressure support device.

Patient circuit 18 has a first end portion 20 operatively coupled to humidifier 14 and a second end portion 22. A lumen 23 is defined through the patient circuit from the first end portion to the second end portion so that a flow of gas is carried from the humidifier or the pressure generating device to the patient during operation of the gas flow generating system. A patient interface 24, which is typically a mask, is coupled to second end portion 22 of patient circuit 18. In the illustrated exemplary embodiment of the present invention, patient interface 24 is a nasal mask. It is to be understood, however, that patient interface 24 can include a nasal mask, nasal pillows, tracheal tube, endotracheal tube, or any other device that communicates a flow of gas from the patient circuit to the airway of the patient.

It is to be understood that various components may be provided in or coupled to the patient circuit. For example, a bacteria filter, pressure control valve, flow control valve, sensor, meter, pressure filter, humidifier, and/or heater can be provided in or attached to the patient circuit. Likewise, other components, such as muffler and filters can be provided at the inlet of the pressure generating device.

Gas flow delivery system 10 shown in FIG. 1 is a single-limb system, meaning that the patient circuit includes only one gas delivery conduit 20 connecting the patient to the pressure generating device. In a single-limb system, exhaust vent 25 is provided in the patient conduit for venting exhaled gasses from the system. The exhaust vent can be provided on the patient interface device and/or on the patient circuit and can have a wide variety of configurations depending on the desired manner in which gas is to be vented from the pressure support system.

The present invention also contemplates that the gas flow generating system can be a two-limb system, which includes a delivery conduit and an exhaust conduit operatively connected to the airway of the patient. A key difference between a single-limb system and a two-limb system is that in a two-limb system, there is an exhaust conduit that carries exhaust gas from the patient. An exhaust valve is also typically provided at the end of the exhaust conduit distal from the patient. The exhaust valve is normally actively controlled to maintain a desired level of pressure in the system, which is commonly known as positive end expiratory pressure (PEEP). This is accomplished by controlling the flow of exhaust gas from the otherwise closed system.

Patient circuit 18 includes a conduit 26, which is preferably a flexible conduit and a radiant barrier 28. Conduit 26 can be any conventional conduit, such as the 6 foot smooth lumen tubing manufactured by the HTH COMPANIES, Inc. or SMOOTH-BOR and sold by RESPIRONICS, Inc. While conduit 26 is shown as being a corrugated tubing, it is to be understood that conduit 26 could be a cylindrical tubing. Conduit 26 can also have any other shape, i.e., non-cylindrical, so long at it accomplishes the function of carrying a flow of fluid from one place to another. It should also be understood that coupling members can be provided at the ends of the conduit 26 for coupling the patient circuit to the pressure generating device, patient interface, or any other desired component and that these coupling members can have any desired configuration or features.

It is should be clearly understood that heat transfer can take place in three forms: 1) conduction, which is by means of molecular agitation within a material, without any motion of the material as a whole, 2) convection, which is heat transfer by mass motion of a fluid when the heated fluid is caused to move away from the source of heat carrying energy with it, and 3) radiation, which is heat transfer by the emission of electromagnetic waves that carry energy away from the emitting object. It is known to prevent heat loss from a patient circuit by providing an insulating material around the conduit. See, e.g., U.S. Pat. No. 5,623,922. While this prevents heat loss due to convection, it does not address heat loss due to radiation. By being formed from a low emissivity material, radiant barrier 28 specifically attempts to reduce or eliminate heat transfer between the interior of the conduit and the ambient environment due to radiation.

In an exemplary embodiment of the present invention, the radiant barrier is disposed on an external surface 32 of conduit 26. In one embodiment, this is accomplished by providing a foil as the radiant material, where the foil is coupled to the conduit by being wrapped around the conduit or is in the form of a flexible sheath into which the conduit is inserted. It is to be understood that radiant barrier 28 can be coupled to conduit 18 in any conventional manner, such as with hook and loop fasteners, a zipper, straps or any other suitable fastening means. For example, the present invention contemplates that the radiant barrier can be provided in a sleeve or sheath, that has a lengthwise zipper or hook and loop fastener, so that the radian barrier is wrapped around the conduit and then coupled to the conduit by closing the zipper or applying the hook and loop fasteners to one another. Providing radiant barrier 28 on the external surface of the conduit can also be accomplished by providing a low emissivity coating disposed on the surface of the conduit. Any conventional coating technique, such as dipping or spray, can be used to apply the radiant barrier coating on the conduit.

In the illustrated exemplary embodiment, radiant barrier 28 surrounds at least a portion of the external surface of delivery conduit 26. Radiant barrier 28 is formed from a radiant barrier material having a low emissivity, such as a reflective foil, to reduce heat loss from lumen 23 due to radiant energy. Preventing heat loss prevents condensation from forming on an interior surface 30 of conduit 26 by preventing the air in the tube from cooling to the point where it reaches its dew point.

The radiant barrier provides a reflective surface that keeps a high percent of the radiant energy from reaching the interior surface of the insulated body. Radiant barrier fabric is found in protective clothing like that used by firemen or space suits. An example of a fabric suitable for the radiant barrier is the CROSSTECH® S/R fabric. A metalized fabric, such as an aluminized polymer fabric, or an an aluminized polymer film is also highly effective as a radiation barrier. Examples of such fabrics include the ClearDome Solar Thermal Barrier Fabric.

Figure 4:
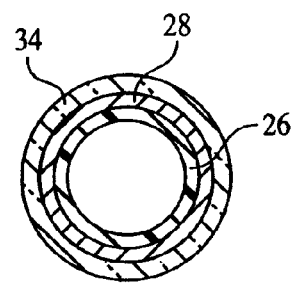
FIGS. 4-7 are cross-sectional views of other embodiments for a patient circuit having a radiant barrier according to the principles of the present invention.

A further embodiment of the present invention contemplates providing a thermal insulation layer 34 over radiant barrier 28. See FIG. 4. Insulating layer 34 is formed from an insulating material having a low thermal conductivity, such as an insulating man-made material comprising polyester fibers, although any suitable insulating material formed from man made and/or natural fibers could be used. An example of a suitable insulating material is the DuPont® Thermolite® Active material, which is a performance fabric employing a hollow-core fiber technology in which air is used as the insulating material.

Figure 5:
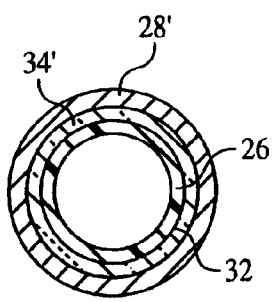

The present invention also contemplates providing a thermal insulation layer 34' disposed between radiant barrier 28' and an external surface 32 of conduit 26. See FIG. 5. Although not shown, another radiant barrier, i.e., low emissivity material, can be provided over thermal insulation layer 34' to further reduce heat transfer. Further layering of thermal insulation materials and radiant barriers can be provided.

Figure 6:
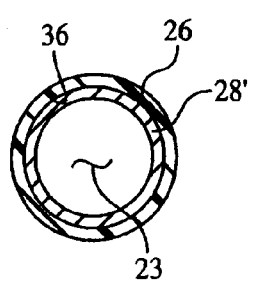
Figure 7:
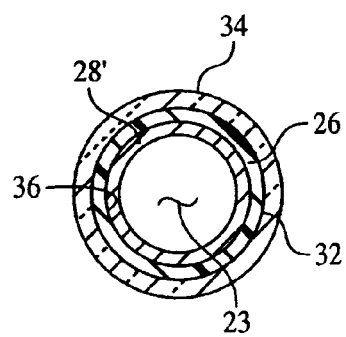
Figure 8:
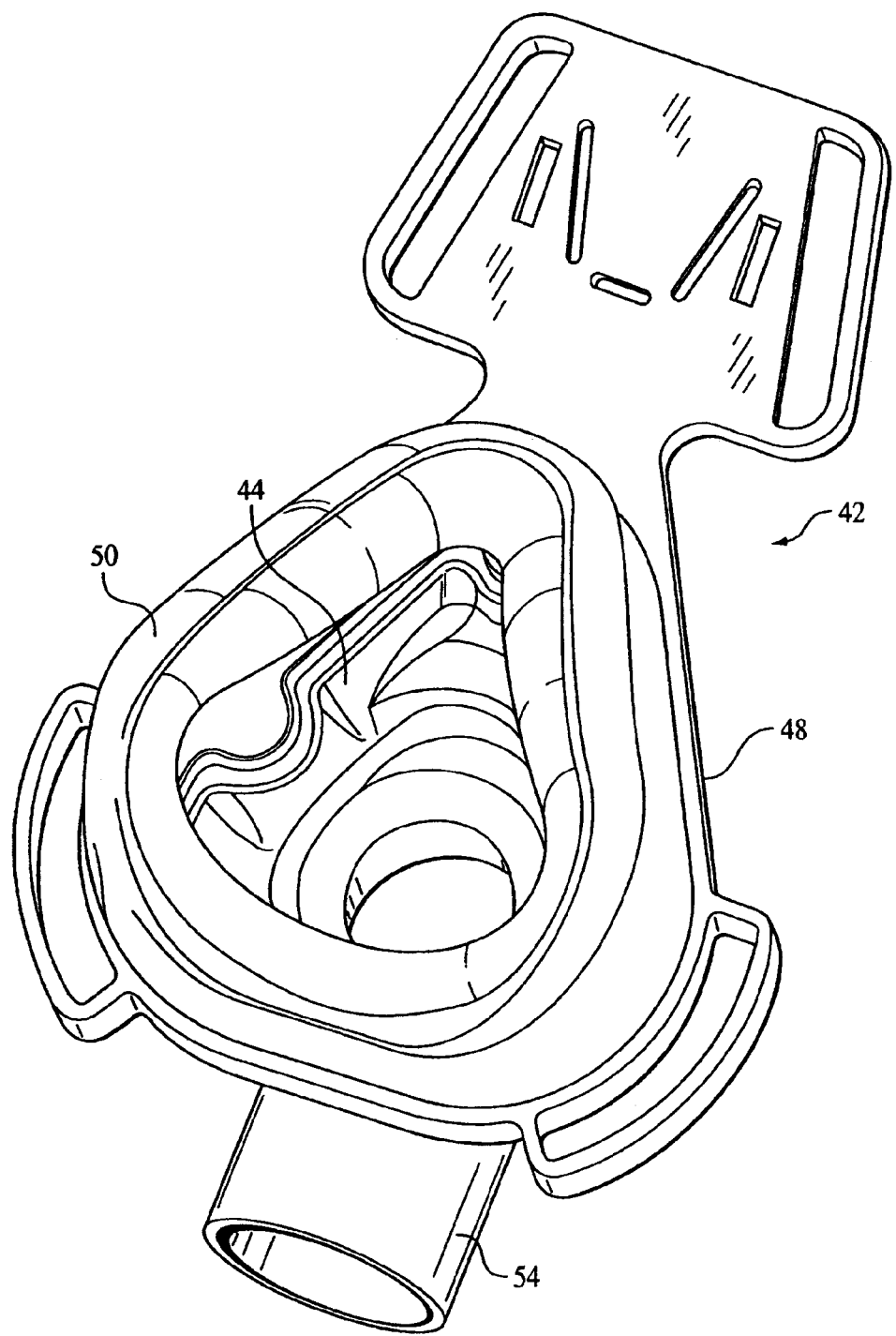
FIG. 8 is a rear perspective view of a first exemplary embodiment of a patient interface having a water trap according to the principles of the present invention.
Figure 9:
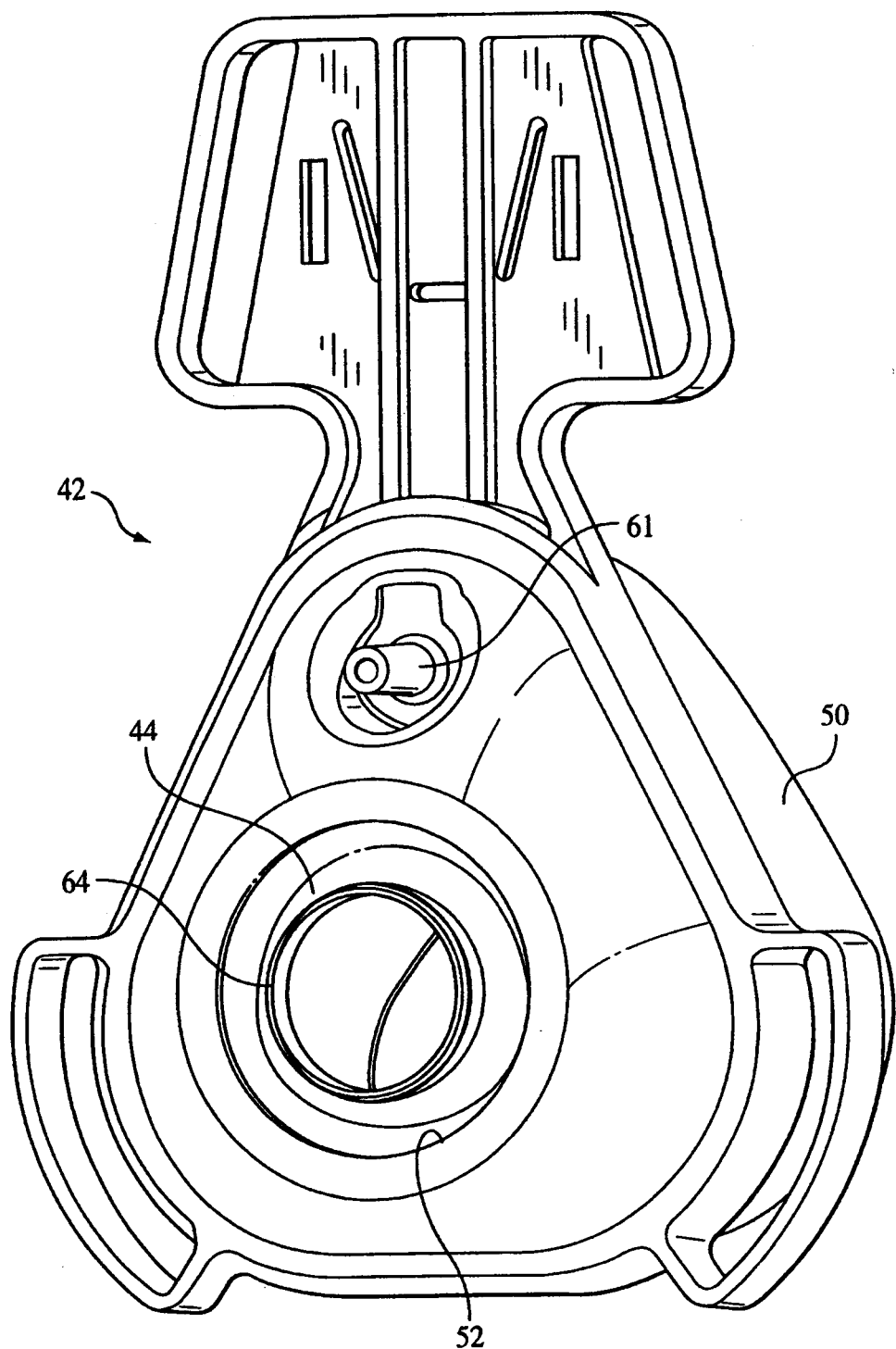
FIG. 9 is front perspective view of the patient interface of FIG. 8.
Figure 10:
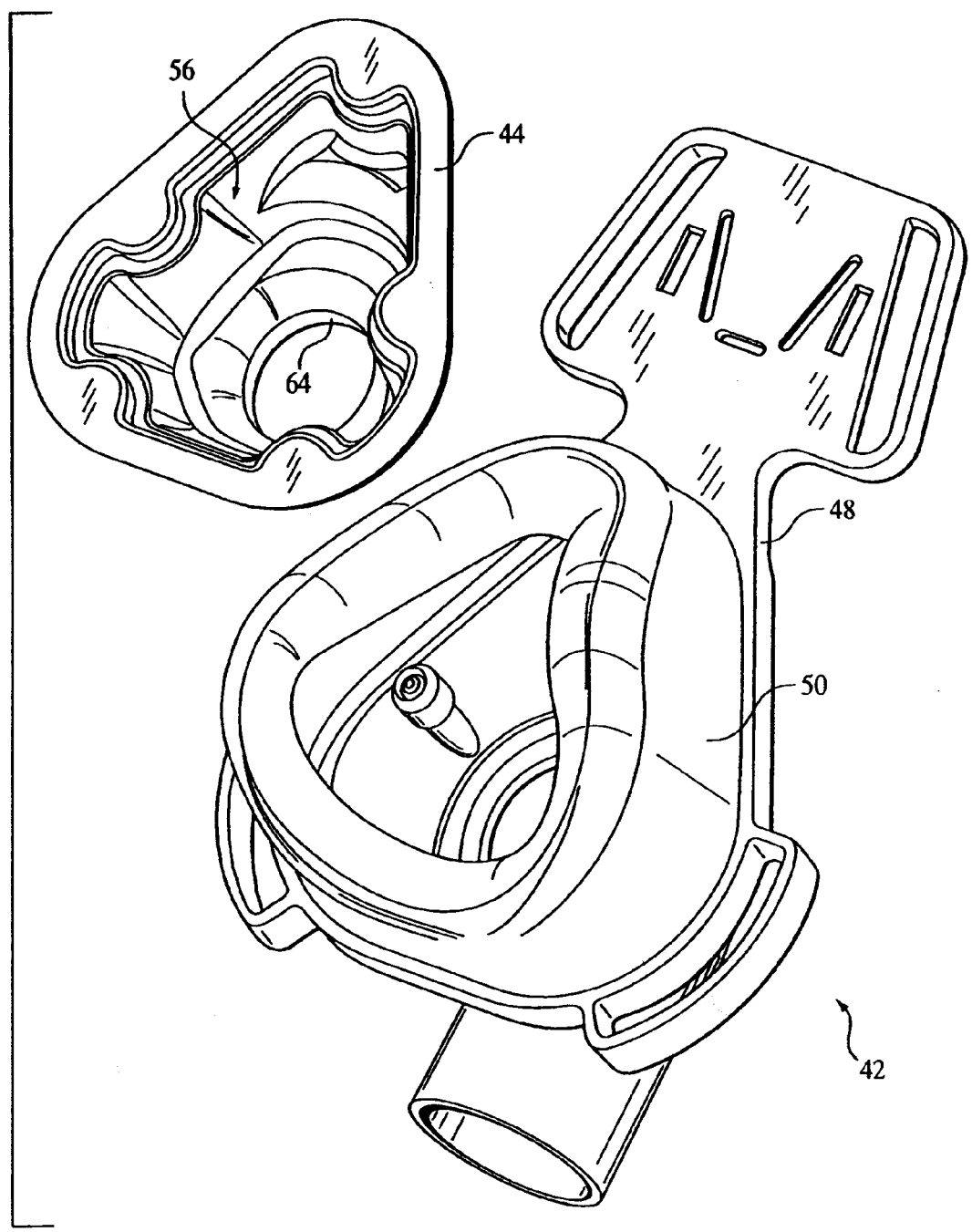
FIG. 10 is an exploded view of the patient interface of FIG. 8.
Figure 11:
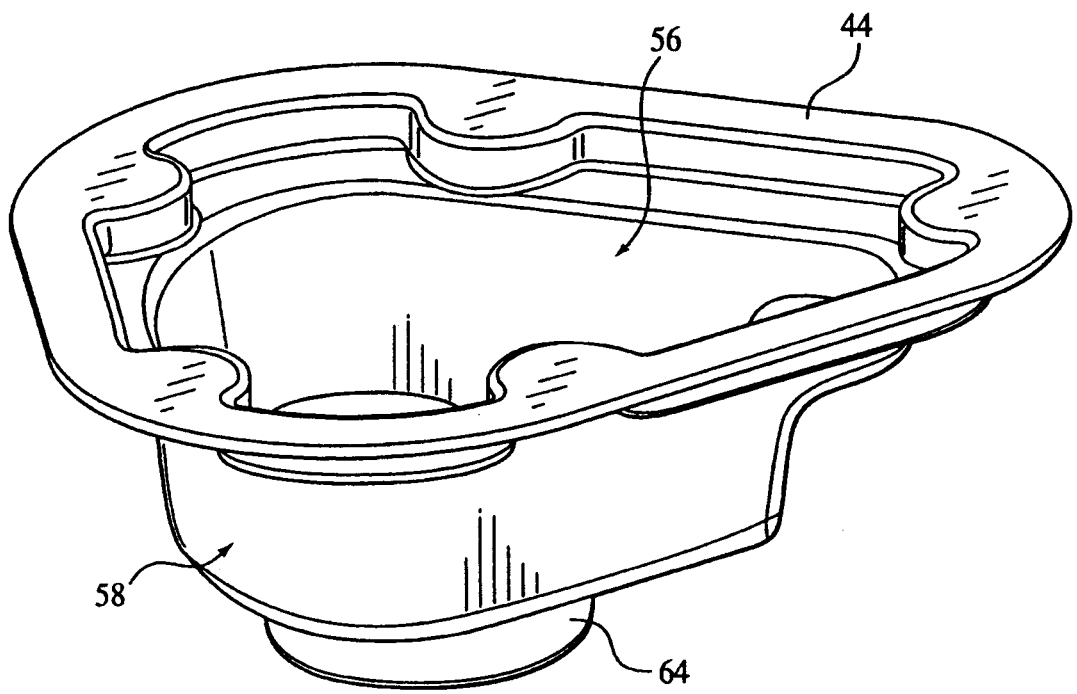
FIGS. 11 and 12 are perspective views of a water trap insert in the patient interface of FIG. 8.
Figure 12:
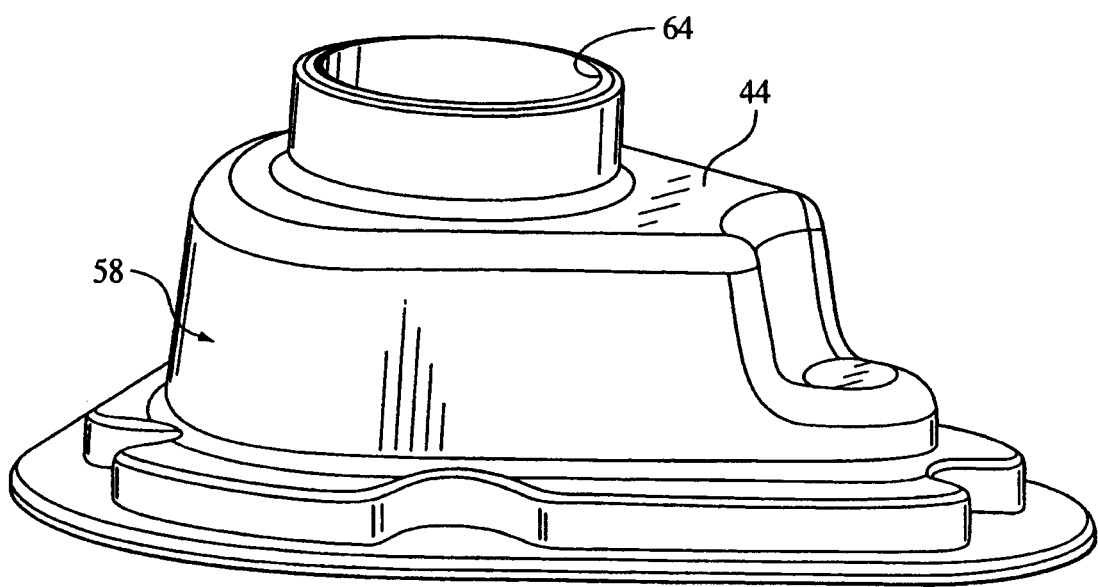
Figure 13:
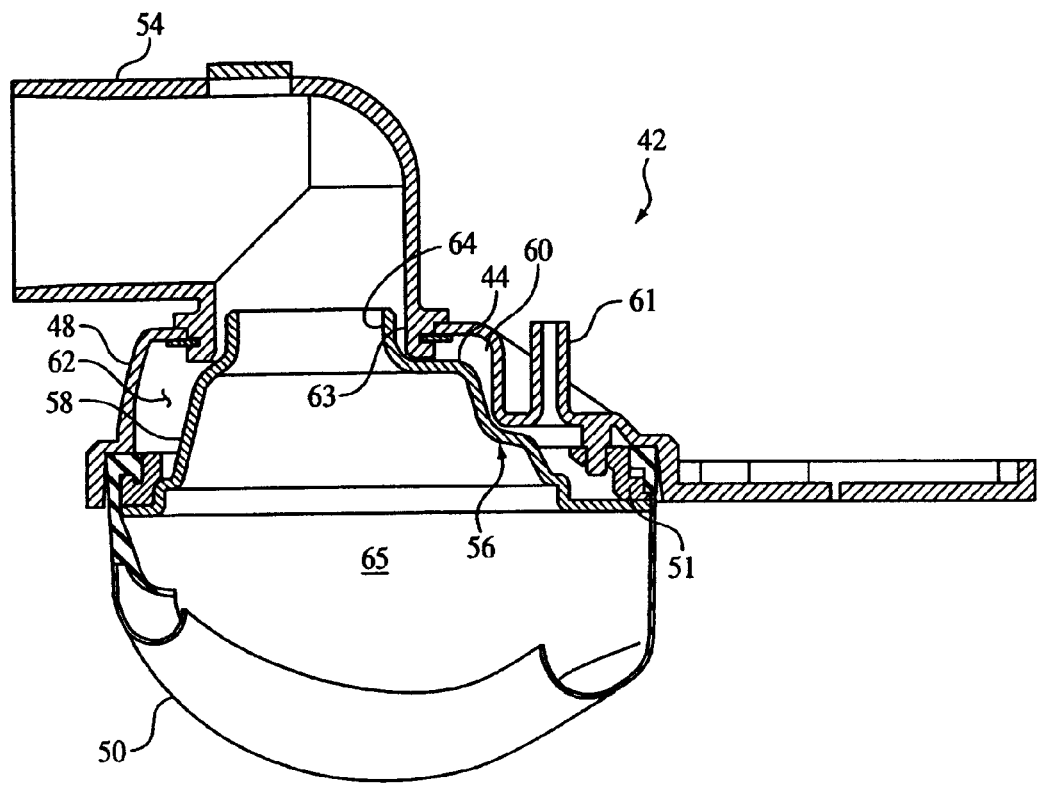
FIGS. 13 and 14 are cross-sectional views of the patient interface of FIG. 8 showing the condensation collection technique.
Figure 14:
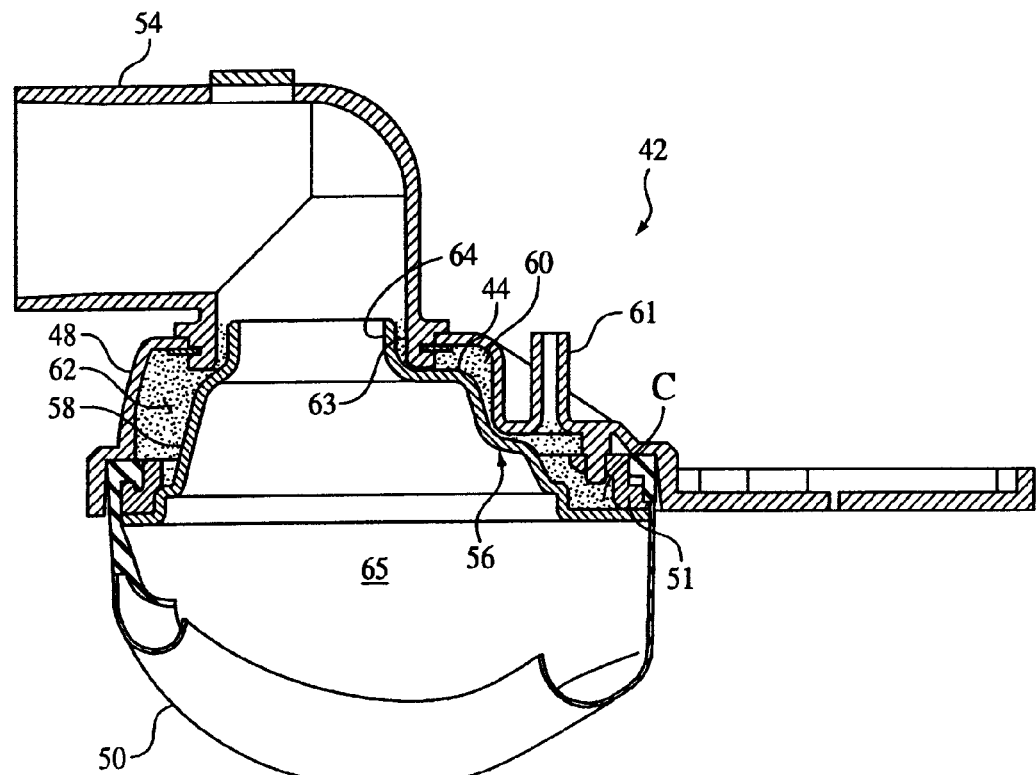
Figure 15:
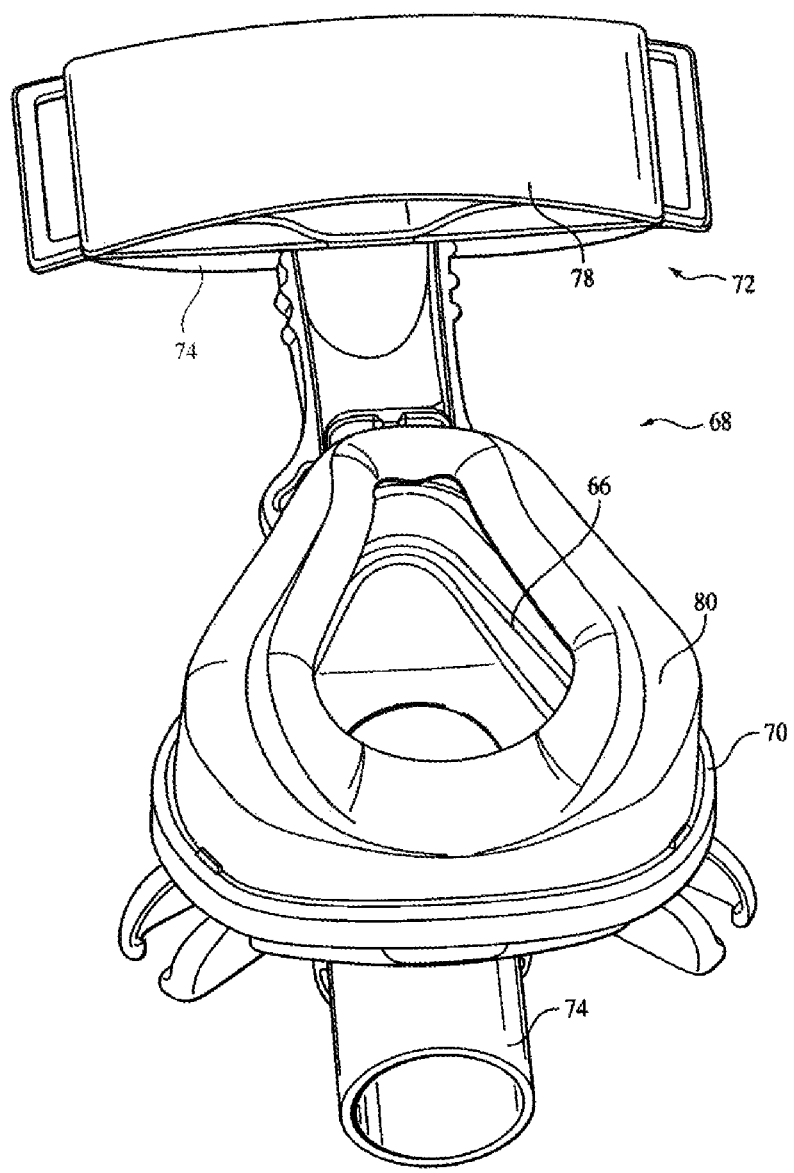
FIG. 15 is a rear perspective view of a second exemplary embodiment of a patient interface having a water trap according to the principles of the present invention.
Figure 16:
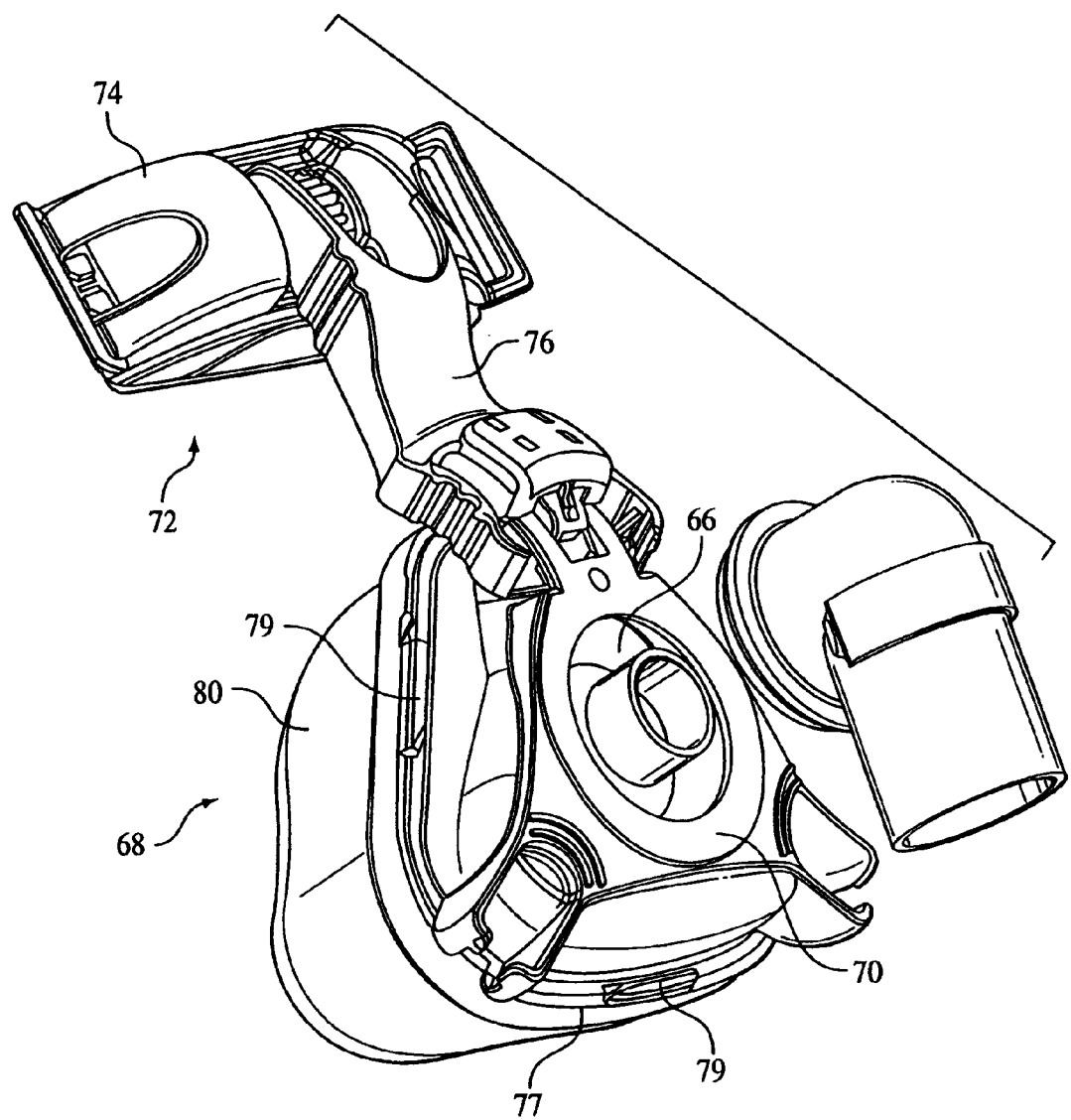
FIGS. 16 and 17 are partially exploded front and rear perspective views, respectively, of the patient interface of FIG. 15.
Figure 17:
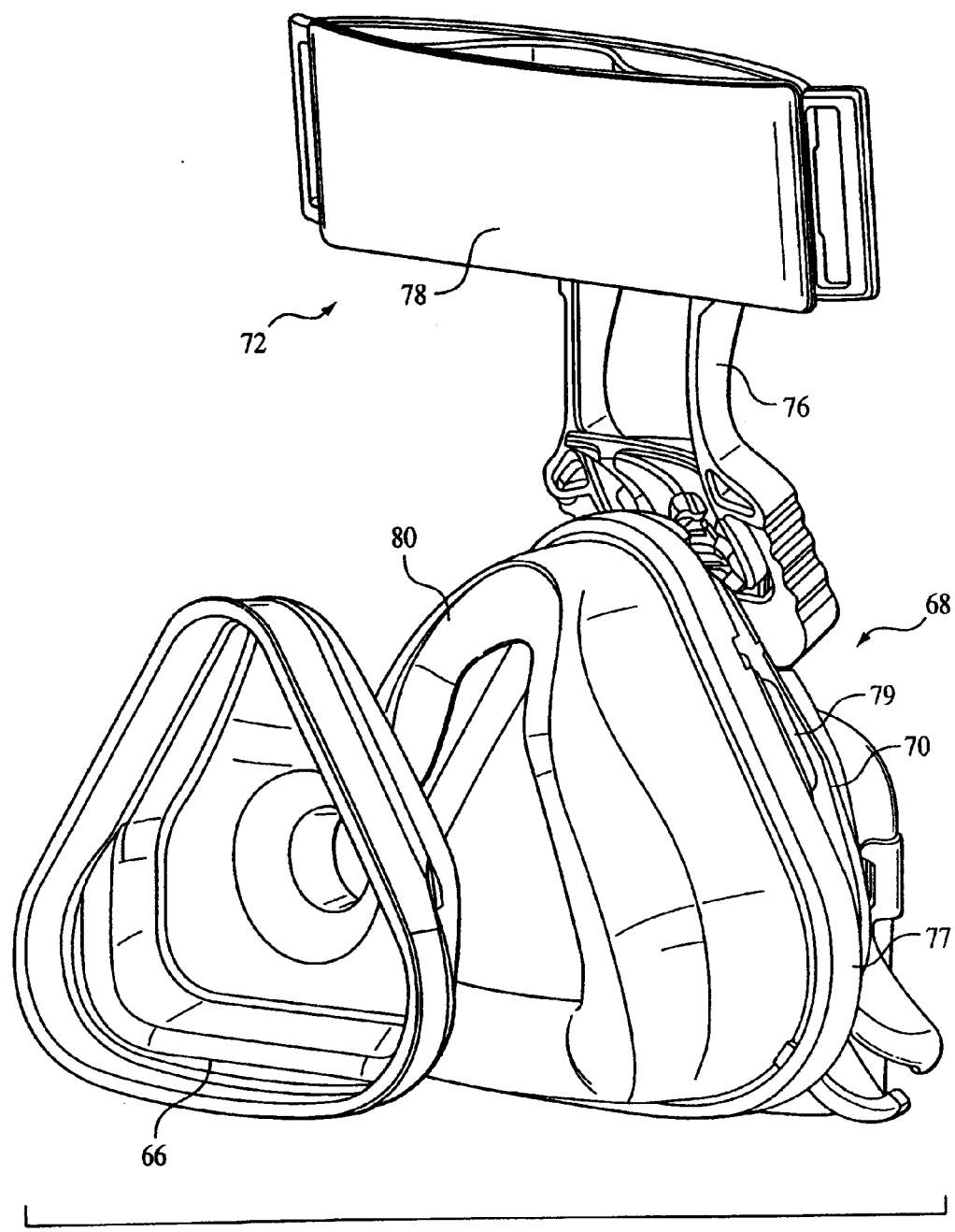
Figure 18:
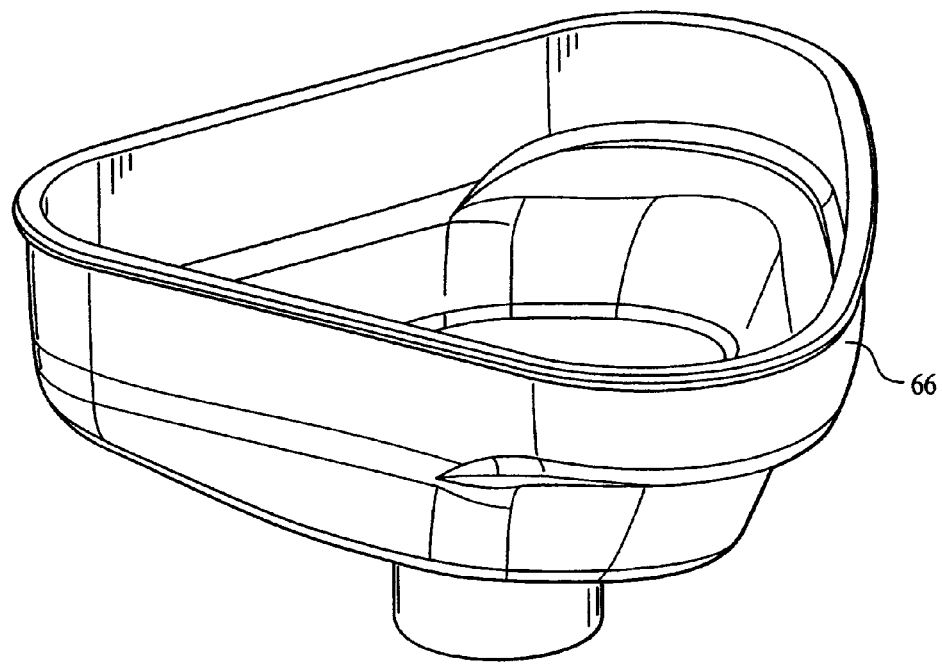
FIGS. 18 and 19 are perspective views a water trap insert in the patient interface of FIG. 15.
Figure 19:
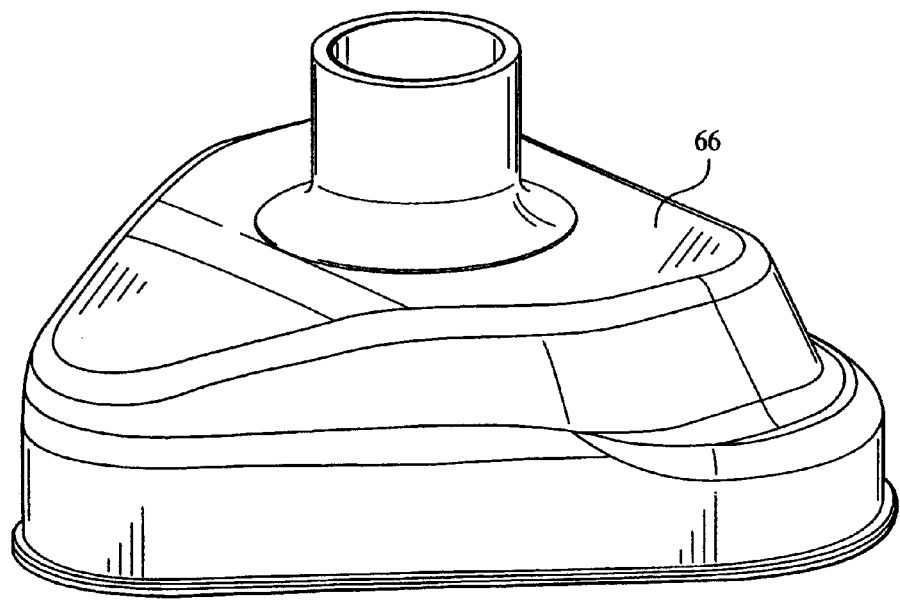
Figure 20:
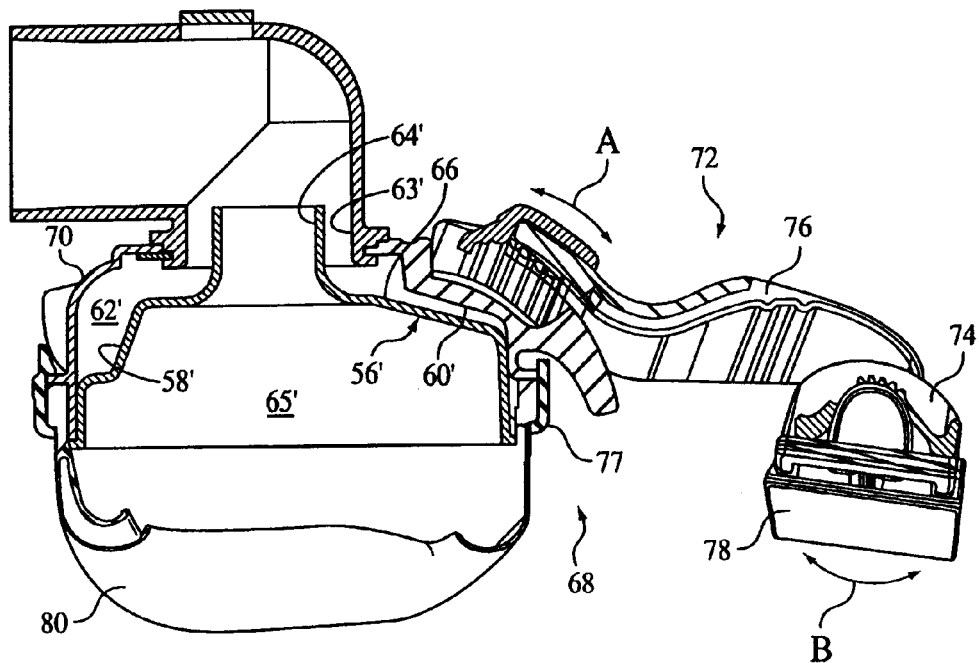
FIGS. 20 and 21 are cross-sectional views of the patient interface of FIG. 15 showing the condensation collection technique.
Figure 21:
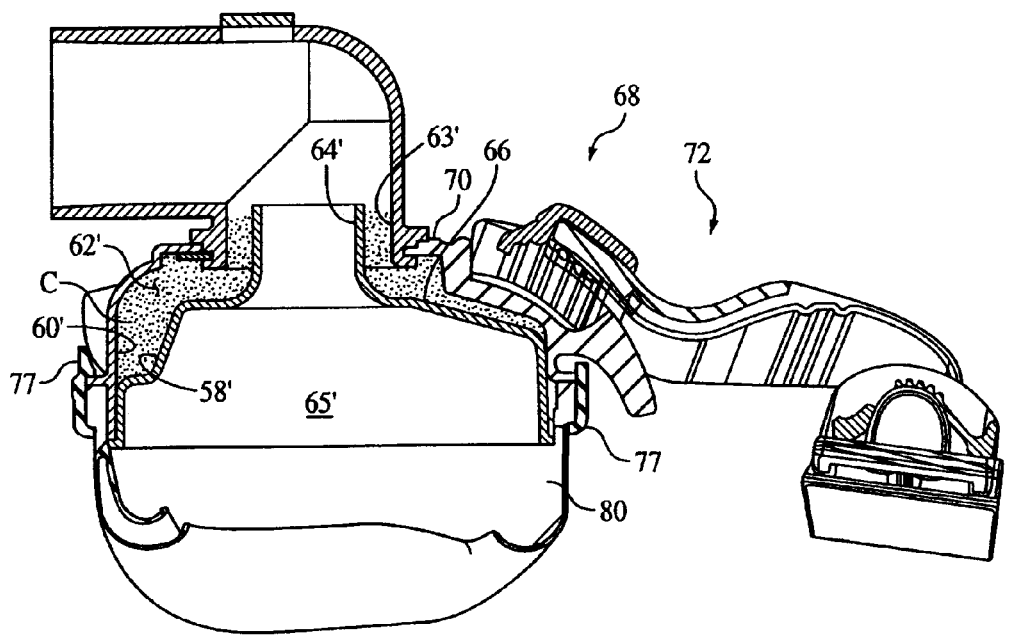

A still further embodiment of the present invention contemplates providing a radiant barrier 28' on an interior surface 36, i.e., a surface facing lumen 23, of conduit 26. See FIGS. 6 and 7. An additional layer of thermal insulation 34' can be provided over external surface 32 of the conduit. See FIG. 7. Of course, further layers of the radiant barrier and/or the thermal insulation can be provided around the conduit. As with the previous embodiment, the present invention contemplates that the radiant barrier can be disposed on or proximate to the interior surface of the conduit using any conventional technique, such as spraying or dipping to coat the radiant barrier on the conduit or by mechanically fastening the radiant barrier to the conduit. The present invention also contemplates that the conduit itself, including the interior and/or exterior surface, can be formed from a low emissivity material, so that the radian barrier is integral with the material defining the conduit.

The present invention contemplates that the radiant barrier can be applied to selected portions of the patient circuit or over the entire patient circuit, i.e., from the outlet of the humidifier 14 and/or pressure generating device, to the inlet of the patient interface device. The present invention also contemplates that the radiant barrier need not be disposed entirely around the conduit, as shown in the figures, but can be disposed around only a portion of the conduit.

Referring now to FIGS. 8-14, a first exemplary embodiment of a patient interface 42 having a water trap according to the principles of the present invention is illustrated. Patient interface 42 includes a mask faceplate or shell 48 and a mask seal 50, also typically referred to as a cushion, for contacting the facial surface of a patient. Shell 48 includes an opening 52, as perhaps best shown in FIG. 9, that communicates with a mask elbow 54 leading to the patient circuit. Patient interface 42 also includes an insert member 44 disposed in a chamber defined by the shell and/or the seal. The present invention contemplates that insert member 44 is either permanently coupled to the shell and/or seal or is electively attachable to either of these components. In addition, the present invention contemplates that mounting components can be used to couple the insert member to the shell or seal so that the insert member is not "directly" attached to either of these components. In the illustrated embodiment, a retaining ring 51 is provided that attaches seal 50 and insert member 44 to shell 50 by fitting into a groove defined in the shell.

Insert member 44 is preferably a contoured cup-shaped member having an inner surface 56 facing the patient and an outer surface 58 facing an inner surface 60 of shell 48. Outer surface 58 is substantially contoured to generally correspond to the shape of inner surface 60 of shell 48. When insert member 44 is in position, a gap 62 is formed between outer surface 58 of the insert member and the inner surface 60 of the shell. Gap 62 functions as a reservoir to segregate or collect condensation C so that the condensation does not reach the patient. A port 61 is defined in shell 48 that communicates gap 62 with an area external to the shell. Port 61 provides a drainage point so that condensation collecting in gap 62 can be removed. Of course, a cap (not shown) can be disposed over the external opening of port 61 to seal the water trap, i.e., prevent fluid from existing port 61.

In this illustrated exemplary embodiment, insert member 44 is substantially triangularly-shaped as is shell 48 and has an opening 64 to allow gas from the patient circuit to pass into a chamber 65 defined by the insert and seal. In an exemplary embodiment, openings 63 and 64 are substantially aligned. Condensation forming on a wall of the patient circuit, i.e., a wall of elbow 54, will travel along the wall of the elbow and enter the shell through opening 63. Because opening 64 of insert member 44 is offset from opening 63 over the entire periphery of these openings, condensation will not enter opening 64, but will pass between openings 63 and 64 into chamber 62.

It should also be noted that gas that is typically warmer than the ambient environment will occupy gap 62. As a result, it is possible that a temperature difference will exist between gap 62 and the ambient environment, which will result in condensation forming on surface 60 of shell 48. Of course, this condensation will be trapped in gap 62. However, there will be little temperature differential between the gas in gap 62 and the gas in chamber 65. As a result, it is unlikely that condensation will form on inner surface 56 or insert member 44 or on the inner surface of seal 50, which is where condensation is most undesired. It can thus be appreciated that the water trap configuration of the present invention not only helps contain any condensation that forms in the patient circuit or the patient interface, but also helps prevent any condensation from forming on any surface that directly faces the surface of the patient.

FIGS. 15-21 show a second exemplary embodiment of a patient interface 68 having a water trap according to the principles of the present invention. Patient interface 68 is similar in many respects to the patient interface shown in FIGS. 8-14; the main differences being in the configurations of a mask shell 70 and insert member 66. More specifically, in this embodiment, mask shell 70 includes an adjustable forehead assembly 72 that is coupled to the mask shell and moves relative to the mask shell, as generally indicated by arrow A in FIG. 20. The forehead assembly also includes a moveable forehead pad support 74 that moves relative to a forehead arm 76, as indicated by arrow B in FIG. 20. A pad 78 is provided on the forehead pad support 74, and a seal or cushion 80 is attached to shell 70. Insert member 66 has a more planar wall than in the previous embodiment. In this embodiment a retaining ring 77 is provided on the outer perimeter of the shell and seal. The retaining ring includes tabs 79 that snap over an edge of the shell to sandwich the edge of the seal between the retaining ring and the shell.

The point to be understood and appreciated is that the present invention contemplates that the various components of the patient interface can have a variety of sizes, shapes, and configurations. For example, any suitable technique can be used to couple the shell, seal, and insert member to one another in either a fixed or separable manner. In addition, other features associated with patient interface devices, such as adjustable forehead supports, headgear connectors, and headgear, can be used conjunction with the water trap condensation management technique.

Figure 22:
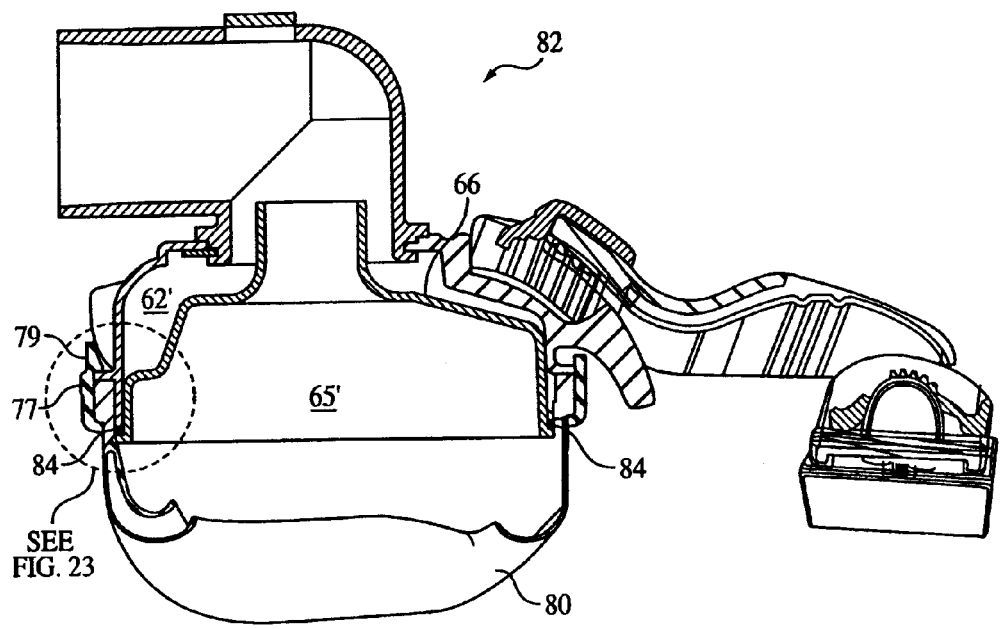
FIG. 22 is a cross-sectional view of the patient interface of FIG. 12 with an additional o-ring.
Figure 23:
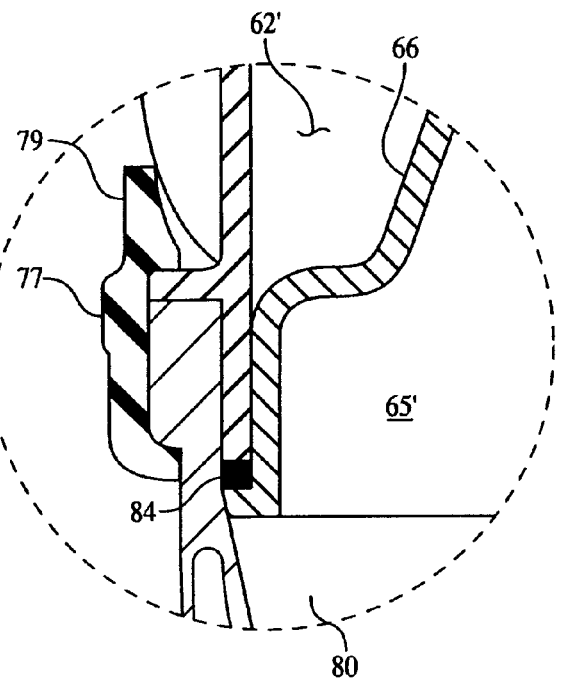
FIG. 23 is a cross-sectional close-up view of the o-ring in the patient interface of FIG. 22.

FIGS. 22 and 23 illustrate a patient interface 82 that is generally similar to patient interface 68. However, patient interface 82 includes an o-ring 84 provided along the outer perimeter of insert member 66. O-ring 84 helps to prevent leakage of condensation from gap 62' into chamber 65'. It should be noted that this o-ring leak prevention feature can be provided on any of the patient interface embodiments of the present invention.

Figure 24:
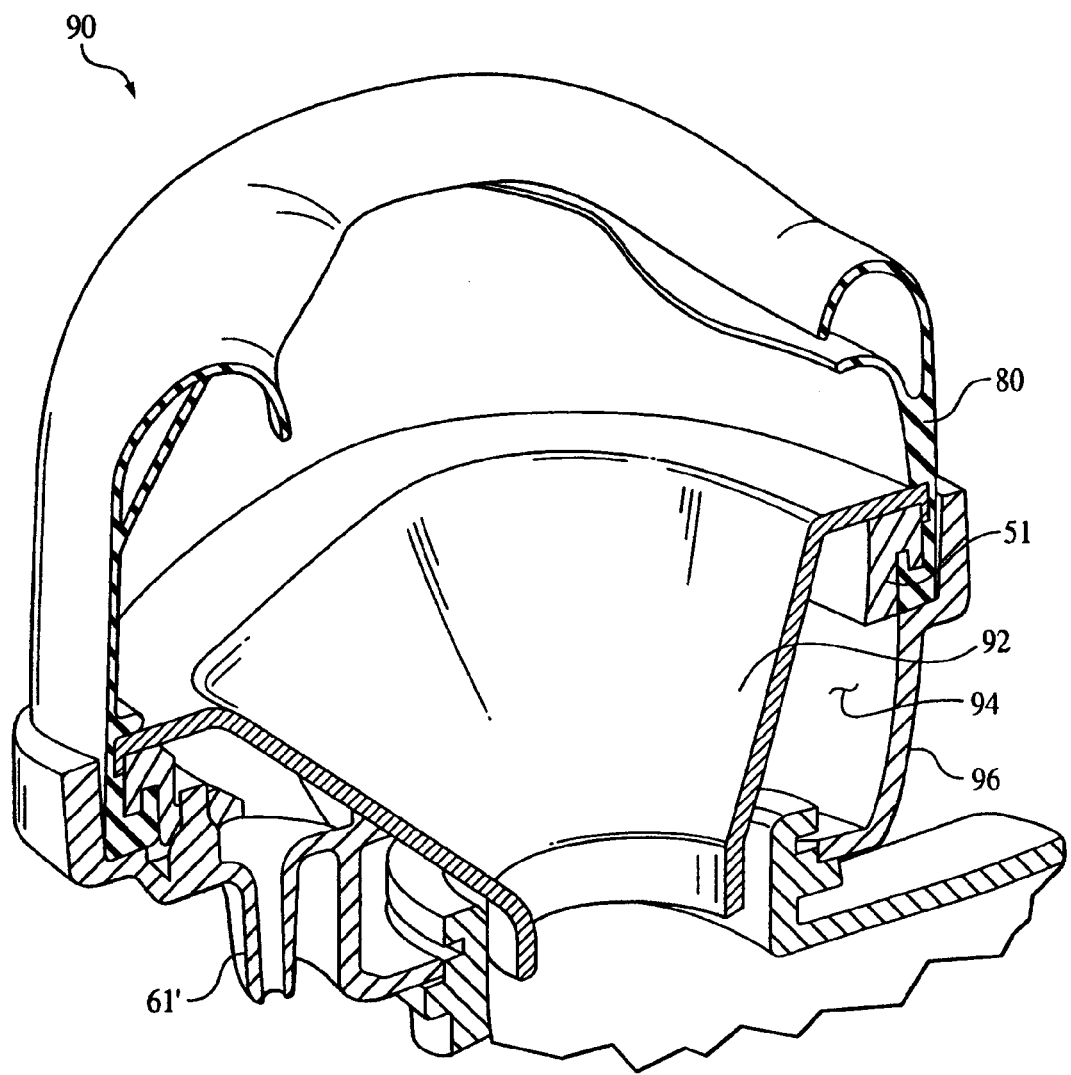
FIG. 24 is a cross-sectional perspective view of a third embodiment for a patient interface having a water trap according to the principles of the present invention.
Figure 25:
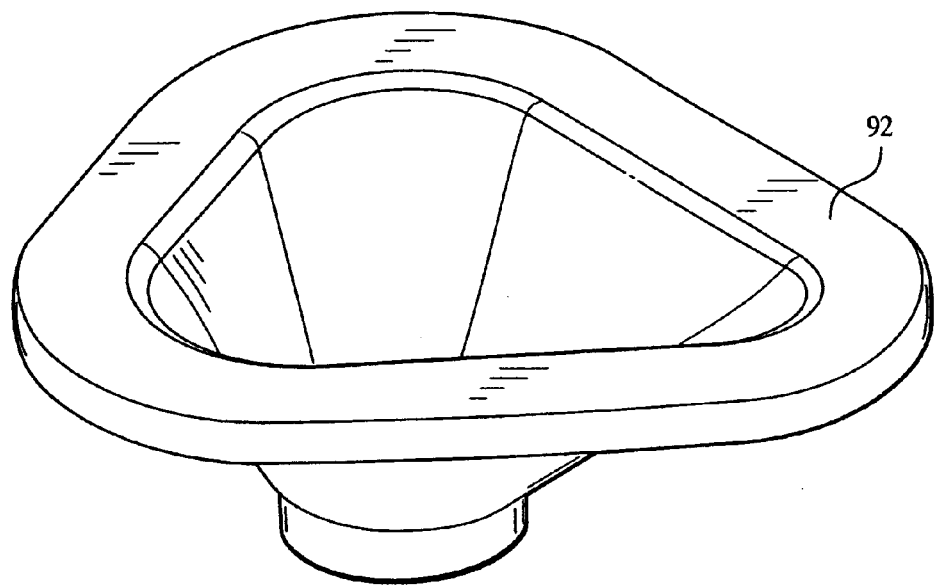
FIGS. 25 and 26 are perspective views a water trap insert for the patient interface of FIG. 24.
Figure 26:
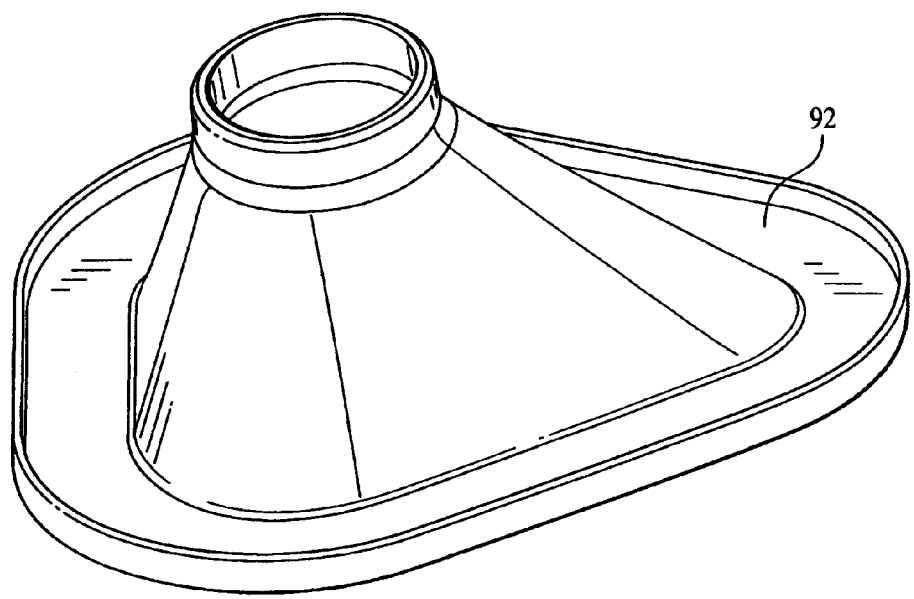

FIGS. 24-26 illustrate a third embodiment of a patient interface 90 having a water trap according to the principles of the present invention. In this embodiment, an insert member 92 is provided to form a water trap gap 94 between the insert member and a wall of shell 96. Insert member 92 is shaped such that the wall or surface of the insert member that faces an interior surface of the shell does not correspond to the shape of the shell. As a result, gap 94 has a relatively larger volume as compared to the other embodiments.

The present invention contemplates providing a thermal insulator insert in the patient interface. In an exemplary embodiment, the insulator insert has a configuration corresponding to the insert members of the previous embodiments. However, the thermal insulator insert need not provide a gap between it and the mask shell wall. For example, the insulator insert can have a shape that substantially matches the inner surface of the shell to provide a thermal insulation barrier in the mask shell that abuts the inner surface of the shell. Of course, the insulator insert can include a gap between it and the wall of the shell. The insulator insert is preferably vacuum formed from a closed cell foam, such as polystyrene foam and may be disposable.

The insulator insert eliminates condensation by reducing the temperature difference between the delivery gas and the ambient environment. The insulator insert creates an air filled barrier to reduce heat loss and lower condensation. The shell material, most typically polycarbonate, has a higher thermal conductivity value than the foam insulator insert. The thermal conductivity of a material is a measure of the ability to transmit heat through the material. The typical value of thermal conductivity for polycarbonate is at 1.44 w/m-k, while the value for polystyrene is 0.202 w/m-k.

Polystyrene foam has a lower thermal conductivity value. In general, the foam insulator insert can reduce heat loss by two-fold.

In yet another embodiment of the present invention, the insulator insert is formed from a low emissivity material to provide a radiant barrier in the shell. The present invention also contemplates providing both a thermal insulator and a radiant barrier in the patient interface. The present invention also contemplates forming the shell of the patient interface from a low emissivity material so that the walls of the patient interface, more specifically, the wall of the shell, form a radiant barrier to prevent heat loss from the chamber in the shell to the ambient atmosphere due to radiation of heat.

Referring now to FIGS. 27-31, another embodiment of the present invention is illustrated. In this embodiment an absorbent insert 100 is located within a chamber defined in a patient interface 102. Preferably the absorbent insert is situated where condensation may form or pool and does not block a patient circuit connection opening 104 defined in the mask shell. Absorbent insert 100 preferably comprises an inner absorbent material 106 disposed within an outer cover 108. Preferably, inner absorbent material 106 is a superabsorbent polymer, such as a polyacrylate absorbent, which is often used in the manufacture of disposable diapers, but may also be any other suitable absorbent material such as cotton. Outer cover 108 is preferably a porous, liquid permeable, material, such as cloth, paper, coffee filter material, tea bag material, or any other suitable material. FIGS. 27-29 illustrate an embodiment in which absorbent insert 100 may be freely manipulated and "dropped in" the interior body portion of the patient interface. The present invention also contemplates that outer cover 108 is formed from an absorbent material.

It is to be understood that the present invention contemplates providing the absorbent insert at other areas of the patient interface and/or patient circuit, such as at the mask shell, mask cushion, the delivery conduit, or the swivel elbow to absorb and isolate condensed water. Alternatively, a secondary component, which contains the absorbent insert, may be connected between the mask and the patient circuit.

In another embodiment illustrated in FIGS. 30 and 31, an absorbent insert 100' is shown having a flexible/formable inner member 110 provided in the interior of absorbent outer cover 108. Flexible/formable member inner member 110 is preferably formed from a moldable shape-retaining material, such as aluminum, copper, brass, a shape memory alloy, or any other shape-retaining metals or alloys or a thermoplastic, such as polycarbonate, polyurethane, polyethylene, or other plastic compounds which allow the absorbent insert to be manipulated and shaped to fit various sizes and styles of patient interfaces. Absorbent insert 100' is placed behind the seal and is held in place by the flexible/formable inner member 110. Absorbent outer cover 108 is formed of a durable material to prevent rupture caused by the flexible/formable inner member. The material for cover 108 may be a woven natural fabric such as cotton, silk, wool, burlap or can be a man made fiber such as polyester, rayon or nylon or may be a blend such as cotton-polyester blend. The seams in cover 108 are sewn or heat sealed/adhesive bonded. Alternatively, the inner member may be pre-formed or molded so that it can be inserted into a cavity or other feature custom-molded into a specific mask. In still another embodiment, the absorbent outer cover itself may be formed from a formable, pliable material which provides rigidity to the absorbent insert itself.

It should be understood that the present invention contemplates using each of the condensation reduction and management techniques alone or in combination with one or more of the other condensation reduction and management techniques.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface comprising:
   a shell having a first shell surface, a second shell surface opposite the first shell surface, a first shell opening, and a second shell opening;
   an insert member having a first insert surface facing the first shell surface and a second insert surface adapted to face a user responsive to the patient interface being worn by the user, wherein a gap is defined between the first insert surface and first shell surface;
   an adjustable forehead assembly comprising a movable forehead support pad and a forehead arm, wherein the forehead pad moves relative to the forehead arm, and wherein the adjustable forehead assembly is coupled to the shell and moves relative to the shell; and
   a water absorbent material disposed in the gap.

2. The patient interface of claim 1, wherein the insert member includes a first insert opening defined therein, and wherein the first insert opening and the first shell opening are substantially aligned.

3. The patient interface of claim 1, further comprising a cushion coupled to the second shell surface.

4. The patient interface of claim 1, further comprising a port defined in the shell communicating the gap with an area external to the shell.

5. The patient interface of claim 1, wherein the insert is removably attached to the shell.

6. A patient interface comprising:
   a shell having a first shell surface, a second shell surface opposite the first shell surface, a first shell opening, and a second shell opening;
   an insert member having a first insert surface facing the first shell surface and a second insert surface adapted to face a user responsive to the patient interface being worn by the user, wherein a gap is defined between the first insert surface and first shell surface;
   a chamber having a chamber surface facing the second insert surface; and
   an O-ring, configured to prevent leakage of condensation from the gap into the chamber, disposed along a perimeter of the insert member.

* * * * *

UNITED STATES PATENT AND TRADEMARK OFFICE
CERTIFICATE OF CORRECTION

PATENT NO. : 9,707,365 B2
APPLICATION NO. : 14/284885
DATED : July 18, 2017
INVENTOR(S) : Doug L. Davidowski et al.

Page 1 of 1

It is certified that error appears in the above-identified patent and that said Letters Patent is hereby corrected as shown below:

In the Specification

Column 1 Line 10-12, delete "61/637,339" and insert --60/637,339--.

Signed and Sealed this
Twentieth Day of March, 2018

Andrei Iancu
*Director of the United States Patent and Trademark Office*